United States Patent [19]
Zadno-Azizi et al.

[11] Patent Number: 6,068,623
[45] Date of Patent: May 30, 2000

[54] HOLLOW MEDICAL WIRES AND METHODS OF CONSTRUCTING SAME

[75] Inventors: Gholam-Reza Zadno-Azizi, Newark; Ketan P. Muni, San Jose; Celso J. Bagaoisan, Union City, all of Calif.

[73] Assignee: Percusurge, Inc., Sunnyvale, Calif.

[21] Appl. No.: 08/812,876

[22] Filed: Mar. 6, 1997

[51] Int. Cl.[7] .................................................. A61M 25/00
[52] U.S. Cl. ........................ 604/530; 604/96; 604/523; 600/585
[58] Field of Search .............................. 604/96, 101, 103, 604/264, 280, 281, 282, 265, 523, 530, 524; 600/585

[56] References Cited

U.S. PATENT DOCUMENTS

| | | | |
|---|---|---|---|
| 3,144,868 | 8/1964 | Jascalevich | 128/350 |
| 3,890,977 | 6/1975 | Wilson . | |
| 4,345,602 | 8/1982 | Yoshimura et al. | 128/349 R |
| 4,445,892 | 5/1984 | Hussein et al. | 604/101 |
| 4,468,216 | 8/1984 | Muto | 604/43 |
| 4,511,354 | 4/1985 | Sterling | 604/98 |
| 4,573,966 | 3/1986 | Weikl et al. | 604/53 |
| 4,655,746 | 4/1987 | Daniels et al. . | |
| 4,665,906 | 5/1987 | Jervis . | |
| 4,748,982 | 6/1988 | Horzewski et al. | 128/344 |
| 4,758,222 | 7/1988 | McCoy . | |
| 4,838,268 | 6/1989 | Kieth et al. | 128/344 |
| 4,881,981 | 11/1989 | Thoma et al. . | |
| 4,911,163 | 3/1990 | Fina | 606/127 |
| 4,925,445 | 5/1990 | Sakamoto et al. . | |
| 4,935,068 | 6/1990 | Duerig . | |
| 4,946,466 | 8/1990 | Pinchuk et al. . | |
| 4,964,409 | 10/1990 | Tremulis | 128/657 |
| 4,998,917 | 3/1991 | Gaiser et al. | 604/96 |
| 5,025,799 | 6/1991 | Wilson . | |
| 5,035,686 | 7/1991 | Crittenden et al. | 604/96 |
| 5,059,178 | 10/1991 | Ya | 604/101 |
| 5,067,957 | 11/1991 | Jervis . | |
| 5,069,226 | 12/1991 | Yamauchi et al. . | |
| 5,120,308 | 6/1992 | Hess . | |

(List continued on next page.)

FOREIGN PATENT DOCUMENTS

| | | |
|---|---|---|
| 0 491 349 A2 | 6/1992 | European Pat. Off. . |
| 0 631 792 A1 | 4/1995 | European Pat. Off. . |
| WO 90/13329 | 11/1990 | WIPO . |
| WO 96/15824 | 5/1996 | WIPO . |
| WO 97/11735 | 4/1997 | WIPO . |

*Primary Examiner*—Corrine McDermott
*Assistant Examiner*—Cris L. Rodriguez
*Attorney, Agent, or Firm*—Knobbe, Martens, Olson & Bear, LLP

[57] ABSTRACT

The present invention provides an apparatus for performing angioplasty or vascular intervention procedures. The apparatus of the present invention comprises a catheter apparatus comprised of a superelastic hollow guidewire, a balloon member and a flexible tip. The superelastic hollow guidewire of the invention is preferably a hypotube of nitinol alloy. The use of nitinol alloy as hollow guidewire provides a catheter apparatus having high flexibility and torqueability as well as small cross sectional diameter.

1 Claim, 10 Drawing Sheets

U.S. PATENT DOCUMENTS

| | | | |
|---|---|---|---|
| 5,163,906 | 11/1992 | Ahmadi | 604/101 |
| 5,167,239 | 12/1992 | Cohen et al. | |
| 5,169,386 | 12/1992 | Becker et al. | 604/49 |
| 5,184,627 | 2/1993 | de Toledo | 128/772 |
| 5,209,727 | 5/1993 | Radisch, Jr. et al. | 604/96 |
| 5,211,636 | 5/1993 | Mische | 604/264 |
| 5,221,270 | 6/1993 | Parker | 604/282 |
| 5,279,546 | 1/1994 | Mische et al. | 604/22 |
| 5,281,200 | 1/1994 | Corso, Jr. et al. | 604/96 |
| 5,322,508 | 6/1994 | Viera | 604/52 |
| 5,324,259 | 6/1994 | Taylor et al. | 604/96 |
| 5,344,402 | 9/1994 | Crocker | 604/96 |
| 5,387,225 | 2/1995 | Euteneuer et al. | 606/194 |
| 5,403,274 | 4/1995 | Cannon | 604/9 |
| 5,411,476 | 5/1995 | Abrams et al. | |
| 5,417,658 | 5/1995 | Loney et al. | 604/96 |
| 5,423,742 | 6/1995 | Theron | 604/28 |
| 5,439,000 | 8/1995 | Gunderson et al. | 128/664 |
| 5,449,343 | 9/1995 | Samson et al. | 604/96 |
| 5,451,209 | 9/1995 | Ainsworth et al. | 604/96 |
| 5,456,667 | 10/1995 | Ham et al. | 604/107 |
| 5,462,529 | 10/1995 | Simpson et al. | 604/101 |
| 5,476,450 | 12/1995 | Ruggio | 604/93 |
| 5,496,346 | 3/1996 | Horzewski et al. | 606/194 |
| 5,500,180 | 3/1996 | Anderson et al. | 264/532 |
| 5,522,800 | 6/1996 | Crocker | 604/96 |
| 5,567,203 | 10/1996 | Euteneuer et al. | 604/96 |
| 5,706,826 | 1/1998 | Schwager | 128/772 |

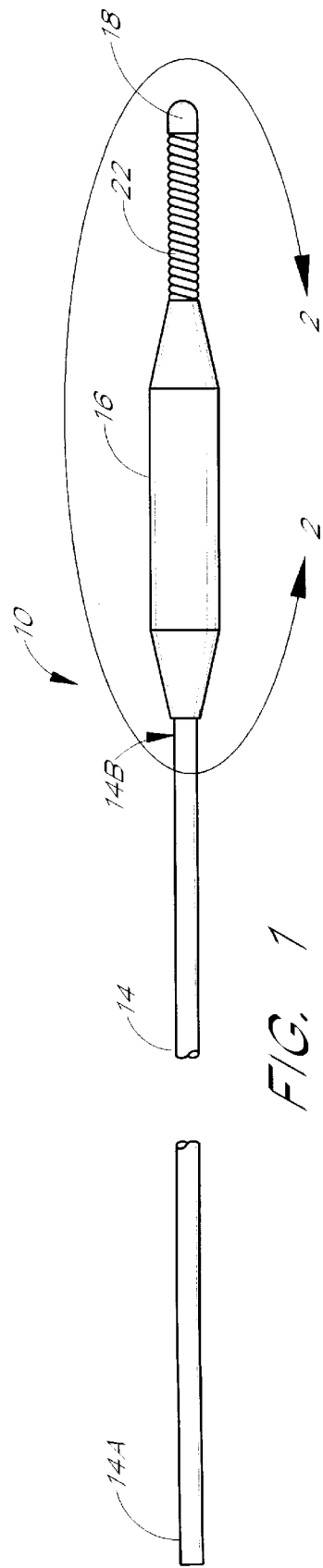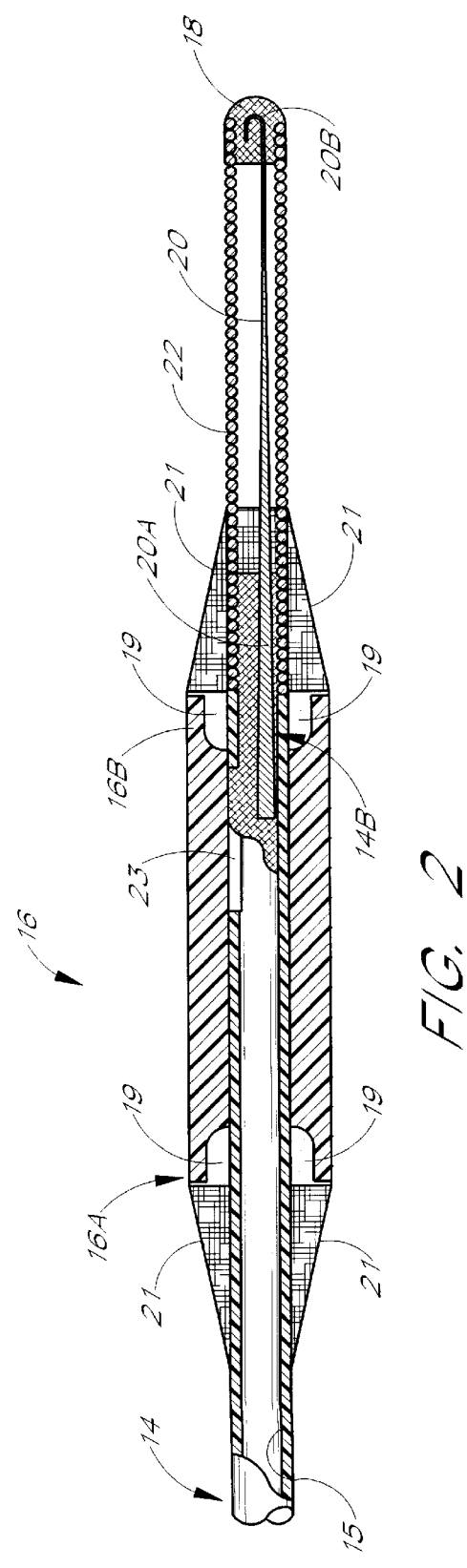
FIG. 1
FIG. 2

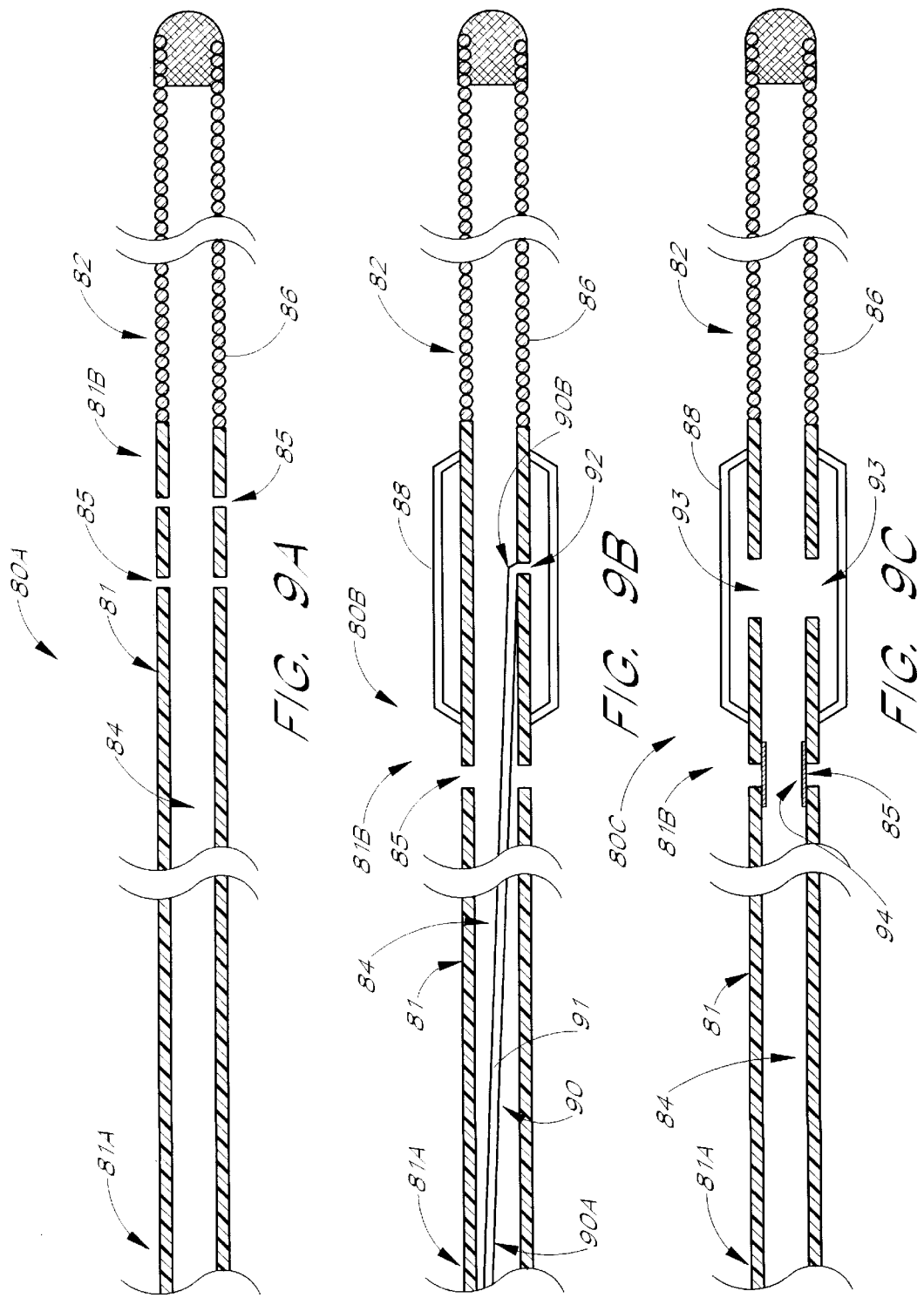

HOLLOW MEDICAL WIRES AND METHODS OF CONSTRUCTING SAME

BACKGROUND OF THE INVENTION

1. Field of Invention

The present invention generally relates to surgical device design and fabrication and, more particularly, to hollow medical wires used as guidewires, catheters, and the like, and methods of constructing same.

2. Description of the Related Art

In the medical community, the continuing trend of less-invasive and noninvasive surgical techniques is driving the medical industry to explore new materials and processes for fabricating surgical instruments and devices having smaller size and better material properties. Examples of such instruments include angioplasty catheters incorporating balloons to dilate an occluded blood vessel. Other catheters are used to deploy stents or other types of therapeutic devices.

Because of the success and acceptance of procedures which utilize such catheters, new procedures are being developed which require variations and adaptations of previous catheter technology. For example, in the U.S., one of the more common applications for medical catheter technology is the "over-the-wire" balloon angioplasty catheter. In this application, the catheter is comprised of an elongate hollow body which has mounted on its distal end an inflatable therapy balloon. The catheter body in this case is typically constructed from a plastic material and is hollow (e.g., sometimes referred to as "microtubing"), both to supply inflation fluids to the balloon and to allow the catheter device to ride over a thin wire to the site to be treated. Thus, this medical device is referred to as an "over-the-wire" therapy catheter.

The thin wire over which the catheter rides is commonly referred to as a "guidewire," obviously, because it guides the therapy balloon to the treatment location. Such medical guidewires are typically made from a solid construction, i.e., they are not normally hollow since they do not need to carry fluids to the therapy site. Such medical wires can be adapted to guide other types of therapy devices well, such as stents, atherectomy devices, laser devices, ultrasound devices, drug delivery devices, and the like.

Another type of balloon angioplasty device is referred to as a "single operator" balloon catheter. More common in Europe, this type of device rides along a guidewire with only a short section of the device (i.e., the "single operator") actually riding completely over with the guidewire.

Another type of therapy balloon device which does not require a guidewire is referred to as a "balloon-on-a-wire" or a "fixed-wire balloon" catheter. The body of the catheter in this case is typically a hollow metallic wire (e.g., a "hypotube") or plastic wire, providing inflation fluid to the balloon mounted on the distal end. This type of therapy balloon device is less common in the U.S., being used in about less than 5% of the angioplasty procedures which are performed, compared with both over-the-wire and single operator type therapy balloon catheters which are used about 70% and 25% of the time, respectively.

In order to successfully perform the desired therapy using present catheter technology, there are a number of functional requirements which guidewires must exhibit. These are, not in any particular order of importance, as follows: pushability; trackability; torqueability; flexibility; and handleability. To the extent that a medical guidewire (or a guiding catheter or another similar guiding devices) exhibits one or more of these functional characteristics, it is more likely to be successful, both medically and commercially.

Pushability refers to the ability of a medical guidewire to be efficiently and easily pushed through the vasculature of the patient without damage thereto, but also without getting hung up, blocked, kinked, etc. Excessive force should not be necessary. The relative stiffness or rigidity of the material from which the wire is made is a key mechanical feature of the wire, at least with respect to its pushability. That is, the wire must be stiff enough to be successfully and efficiently pushed through the vessels to the treatment site, but not too stiff to cause damage. Likewise, a guidewire that is not sufficiently stiff or rigid will suffer "prolapse." This condition occurs when the wire bends over on itself or strays down a branching vessel without progressing to its intended site. Thus, a wire that is too limp lacks sufficient strength to have good pushability characteristics, which are important in virtually all guidewire applications.

Trackability, in the case of guidewires, refers to the ability of the wire to have another device, such as a therapy catheter, efficiently pushed over it to a particular location. Thus, this is also an important feature of catheters which must also "track" efficiently over a guidewire. Time is usually of the essence with respect to many noninvasive therapy procedures since the blood flow of the patient may be interrupted partially or wholly, during such therapy. In addition, there are often a number of "exchanges" during such procedures in which one over the wire device is removed and replaced with another—both riding on the same guidewire. Thus, the ability of the guidewire to provide good tracking characteristics is important to the success of the wire. Again, the stiffness of the wire plays an important role in its trackability characteristics. Also, the lubricity of the material from which the wire is made will enhance its trackability by reducing frictional forces.

Torqueability refers to the ability of a medical wire to be accurately turned or rotated. It is often important, in traversing bends or turns, that the wire be rotated into a certain position. Ideally, a guidewire should exhibit 1:1 torqueability characteristics; for example, a one-quarter turn by the physician at the proximal end should result in precisely a one-quarter turn in the wire at the distal end. As one may expect, such ideal torqueability is very difficult to achieve in present medical wire technology.

Flexibility is another important characteristic of medical wires. It relates to the ability of the wire to follow a tortuous path, i.e., winding and bending its way through the tight turns of a patient's vasculature. Small radius turns are found especially in the coronary arteries. Furthermore, diseased blood vessels become even more tortuous. For example, if plastic deformation in the wire results from traversing smaller, tight radius turns, the rigidity of the wire will be reduced. In addition, due to the permanent deformation, the straightness of the material is lost. It is therefore more likely to kink or possibly even break. Moreover, if the distal tip is bent, upon rotation, an injurious effect known as "whipping"

occurs as the distal tip of the wire beats against the inner wall of the vessel. Thus, the ability of a guidewire to traverse such tortuous paths without kinking, deformation, or damage to the vessel walls, is very important.

The handleability of medical wire relates to its feel during use. Especially important are reduced functional characteristics, such that the physician can actually "feel" the tip as it is manipulated (including both torquing and pushing) from the proximal end. The therapeutic procedures using such wires require precise accuracy; thus, the movements of the wire must be smooth, controllable, and consistent. This is especially difficult to achieve in consideration of the long lengths of the wires (approximately 100 cm or more), and the fact that large sections remain outside the body while other sections are in the body and more or less hidden from view. Thus, it is important for the wire to be readily handled by the physician without kinking or requiring excessive forces or awkward movements.

It will also be noted that present guidewire technology also faces the challenge of extremely small dimensions. For example, guidewires used in therapeutic procedures performed in peripheral vessels often have an outer diameter of about 0.035 inches to around 0.038 inches. Wires used in connection with the coronary arteries are even smaller, ranging from 0.014 inches to 0.018 inches OD. Some devices even utilize guidewires with outer diameters of 0.009 inches. With these extremely small dimensions, it is very difficult to maintain the functional requirements for medical guidewires as outlined above.

Moreover, medical guidewires should also meet a number of structural requirements. The straightness of the wire is very important. If it is not as straight as possible, many functional features are lost, including most significantly the risk of damage to the vessel. Moreover, the roundness of the wire contributes to its accurate torqueability. Consistent wall thickness, lubricity, and many other structural and dimensional characteristics also play an important role.

In order to achieve these functional and structural characteristics, various materials have been proposed for the construction of the medical guidewires of the prior art. For the most part, elastic materials such as stainless steel have heretofore been used. Other so-called "superelastic materials" have also been utilized. Elasticity in a material is its ability to recover strain after deformation. High elasticity (or "super elasticity") therefore refers to the ability of the material to undergo deformation and to return to its original configuration without being permanently or "plastically" deformed. When such permanent or plastic deformation occurs, the structural integrity of the material is diminished (e.g., it loses, to some degree, its rigidity, and/or torqueability), and it assumes a new configuration (sometimes referred to as the "permanent set") from which subsequent loading begins. Moreover, the plastic deformation of a superelastic material may be accelerated through a number of cyclical deformations, sometimes referred to as fatigue. Such cyclical deformations can occur if the wire experiences a number of tight turns, such as is possible in the coronary arteries. Such superelastic materials include a variety of nickel titanium (NiTi) alloys, commonly referred to as "nitinol," and other alloys exhibiting similar properties such as Cu—Zn—Mn and Fe—Mn—Si ternary alloys.

In medical guidewire applications, probably the most common of elastic materials is stainless steel. It provides good stiffness characteristics to supply desired pushability and torqueability. However, superelastic materials, including nitinol have also been suggested for medical wire applications. Although such elastic and superelastic materials provide acceptable results for typical applications, there is a need for more versatile and functional guidewires, especially as new therapeutic procedures are developed. In particular, there is a need for hollow medical guidewires which provide a lumen for inflation fluids, drug-delivery, device deployment and the like. As compared to the standard solid construction, such a hollow guidewire would provide much greater functionality or performance.

However, the challenges facing catheter designers today are greatly magnified in the case of a hypotube (even those made from a superelastic material) used to construct hollow guidewires. Furthermore, the adverse conditions experienced in actual practice may have a deleterious effect on the functional characteristics of the hollow wires, particularly those having extremely small diameters and thin wall thicknesses. For medical wire applications, such adverse conditions would include primarily the need to cyclically traverse a number of highly tortuous turns. This bending and twisting may result in plastic deformation which tests the true superelasticity of the material from which the wires are constructed. As a result, patients may suffer certain injuries, the full effects of which may not be known for years.

SUMMARY OF THE INVENTION

The aforementioned needs are satisfied by the medical wire device of the present invention which provides a highly versatile, efficient apparatus for performing angioplasty and other therapeutic procedures. In one embodiment, the present invention comprises a catheter having an elongate hollow body and a distally mounted occlusion device, preferably an occlusion balloon. The catheter body, which serves as a guidewire, comprises a hypotube constructed from a specially selected superelastic nitinol material. The nitinol material exhibits unique non-linear characteristics which provide unexpectedly high guidewire performance features. Moreover, because it is a hollow guidewire, the present catheter can deliver deployment media to the distal occlusion device, or assist in many other functions such as irrigation, drug delivery, and the like.

Thus, it will understood that the terms "catheter" and "guidewire," as used herein with reference to the medical device of the present invention are not to be limiting in any respect to their construction, materials, or functions, since the principals of the present invention are applicable to a wide variety of medical devices. The distal end of the catheters also provide it with a soft tip in order to avoid injury to the patient. Moreover, the body of the catheter, just proximal the occlusion balloon, is provided with a series of spaced radial radiopaque markers in order to provide visible reference points for the physician within the working space.

In another embodiment, the present invention comprises a catheter of similar construction in which the superelastic nitinol body does not necessarily serve as a guidewire. In yet another embodiment, the present invention comprises a composite medical wire device in which the wire is only partially constructed from the preferred non-linear superelastic nitinol material. In this embodiment, in order to achieve certain advantageous performance characteristics, the material may be joined with other materials (such as stainless steel, polymers or plastics, etc.) so as to be utilized for a given application. In a preferred embodiment, the distal section is constructed from the special nitinol material in order to achieve superior performance in softness and elasticity, but other sections may be formed from this material as well. In addition to such composite devices, the elongate body of the catheter can be internally constructed from the preferred nitinol material and then covered with a bilayer of stainless steel to form a concentric construction. Likewise, special heat treatments can be applied to the distal section to provide it with superior softness and flexibility. Also, such flexibility can be achieved through tapering to very small wall thicknesses. Thus, it will be understood that the principals of the present invention can be applied to medical wires of all types, partially or wholly metallic, hollow or nonhollow, etc., which may be used alone or in combination with other devices including therapeutic devices.

The preferred superelastic medical wire comprises a Ni—Ti (nitinol) binary alloy having a nickel content between 50.0% and 51.5% by atomic weight, and preferably about 50.8%. The wire material can also be selected from a group of nitinol family ternary alloys comprising of Ni—Ti—V, Ni—Ti—Co, Ni—Ti—Cu, Ni—Ti—Cr, Ni—Ti—Nb, Ni—Ti—Pd or from a group of non-nitinol ternary alloys comprising Fe—Mn—Si. A catheter or guidewire of the present invention constructed from the selected nitinol material exhibits outstanding performance characteristics. However, in addition, due to the special character of this material, the present invention wire devices also exhibit important characteristics of high recoverable strain and low modulus. Thus, recoverable strains in the range of about 1% to about 8% are feasible. This allows the present medical wire device to undergo high deformation without plastically deforming, a characteristic which is especially important in the case of thin-walled hollow hypotubes.

At the same time, due to the low modulus characteristics of the material, low stresses are induced as the device traverses the tortuous paths of the vasculature of the patient. Because of the low stress forces, reduced frictional forces are experienced; thus, the medical wire device of the present invention provides excellent handleability and "feel" for the physician. In addition, there is reduced risk of injury. Moreover, in one embodiment, the nitinol material undergoes special heat treatment in order to achieve transformational effects. In this case, substantially constant stresses are maintained over a wide range of recoverable strains, improving even further the performance of the device.

Thus, in one embodiment, the present invention comprises a medical guidewire having an elongate body with distal and proximal sections. The body is constructed at least partially from a non-linear, superelastic nickel titanium alloy material having a nickel content in the range of about 50% to 51.5% atomic weight. The distal section of the body receives heat treatments in the range of 300° C.–600° C. for about 10 seconds to 60 minutes such that the material has recoverable strains in the range of about 1% to about 8%. The device also is provided with an occlusion device mounted on its distal section, and a lumen formed in the elongate body for communicating fluids from the proximal section to the distal section of the body. A passage way is formed through the distal section to communicate said fluids to the occlusion device.

In another embodiment, the present invention comprises a medical catheter having an elongate body and having distal and proximal sections. The body is constructed from a nickel titanium alloy material having a nickel content in the range of 50.0%–51.5% by atomic weight. At least the distal section of the body is constructed from a transformational nickel titanium alloy material exhibiting substantially constant stress over a range of recoverable strain from about 1% to about 8%. The device is also provided with a balloon mounted on its distal section and a lumen formed in the elongate body for communicating fluids from the proximal section to the distal section of the body. A passageway is formed through the distal section to communicate fluids to the balloon.

In yet another embodiment, present invention comprises a medical wire having an elongate body with distal and proximal sections. At least the distal section is partially constructed from a nickel titanium alloy material having substantially constant stress values over a range of recoverable strains from about 1% to about 8%. The proximal section is constructed from a second material having a modulus which is different for a given strain than the alloy material.

In yet another embodiment, the present invention comprises a medical wire having an elongate body comprising a hollow non-linear superelastic nickel titanium alloy material having recoverable strain in the range of 1% to at least 8%.

These and other advantages of the present invention will become more fully apparent from the following description taken in conjunction with the accompanying drawings.

BRIEF DESCRIPTION OF THE DRAWINGS

FIG. 1 is a schematic view of the medical catheter of the present invention;

FIG. 2 is a schematic cross-sectional view of a distal portion of the catheter apparatus shown in FIG. 1;

FIGS. 9A–9C are schematic cross-sectional views of alternative embodiments of a hollow catheter having holes, valves, and the like, to permit the escape of irrigation or other fluids.

DETAILED DESCRIPTION OF THE PREFERRED EMBODIMENT

Figure 3:
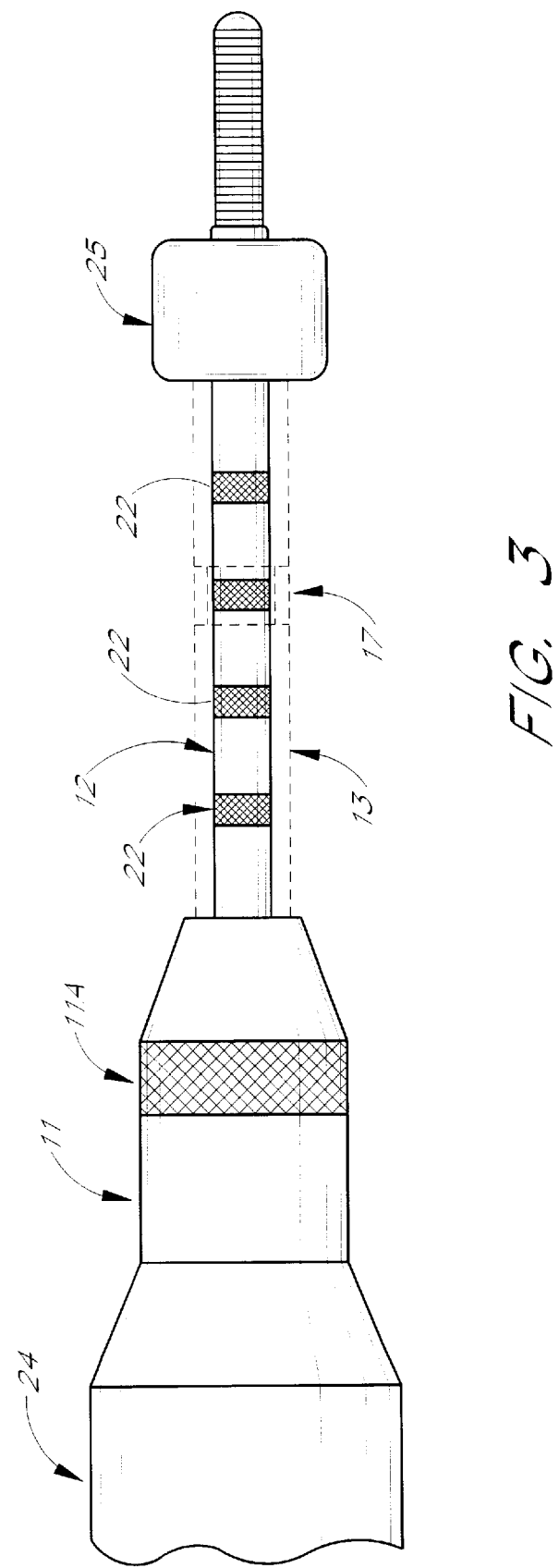
FIG. 3 is a schematic view of a hollow guide wire comprising a series of radiopaque markers.

As will be described hereinbelow the apparatus of one embodiment of the present invention is a catheter apparatus for treatment of stenosis in a lumen in a blood carrying vessel. Although the catheter includes a hollow medical guidewire as illustrated and described, it will be understood that the principles of the present invention apply equally to other types of medical wires and catheters.

Hollow Medical Guidewires

As shown in FIGS. 1–2, the catheter apparatus 10 is generally comprised of four communicating members including an elongated body or tubular member 14, a balloon member 16 and a core-wire member 20 and a coil member 22. The catheter apparatus 10 is preferably provided with an outer coating of a lubricous material, such as Teflon. The body member 14 of the catheter apparatus 10 is in the form of hypotubing and is provided with proximal and distal ends 14A and 14B and as well as an inner lumen 15 extending along the tubular member 14. The balloon member 16 is coaxially mounted on the distal end 14B of the tubular member 14 by suitable adhesives 19 and 21 at a proximal end 16A and a distal end 16B of the balloon member 16 as in the manner shown in FIG. 2. A passageway 23 is formed through the tubular member to communicate fluids to the balloon 16. The core-wire member 20 of the catheter 10 may be comprised of a flexible wire 20. The flexible wire 20 is joined by soldering, brazing or using adhesives at a proximal end 20A of the flexible wire 20 to the distal end 14B of the tubular member 14 as in the manner show in FIG. 2.

Preferably, the proximal end 20A of the flexible wire 20 has a transverse cross sectional area substantially less than the smallest transverse cross-sectional area of the inner lumen 15 of the tubular member 14. In the preferred embodiment, the flexible wire 20 tapers in the distal end 20B to smaller diameters to provide greater flexibility to the flexible wire 20. However, the flexible wire may be in the form of a solid rod or a helical coil or wire ribbon or combinations thereof.

As shown in FIG. 2, the distal end 20B of the flexible wire 20 is secured to a rounded plug 18 of solder or braze at a distal end of the coil member 22. The coil member 22 of the catheter 10 may be comprised of a helical coil. The coil member 22 is coaxially disposed about the flexible wire 20, and is secured to the flexible wire 20 by soldering, brazing or using adhesives at about the proximal end 20A of the flexible wire 20 as in the manner shown in FIG. 2. The balloon member 16 is preferably a compliant balloon formed of a suitable elastic material such as C-Flex™, a latex or the like. Other occlusive or therapy devices could also be used. The flexible coil 22 is preferably formed of a wire of platinum based alloy so as to be visible during fluoroscopy. The flexible core-wire 20 may preferably be formed of a superelastic nickel-titanium alloy or stainless steel. However, the tubular member 14 is preferably formed of a superelastic nickel-titanium alloy described below in more detail. Further details regarding the catheter and its construction are found in co-pending applications all filed on Mar. 6, 1997 and assigned Ser. No. 08/813,024, entitled Catheter Balloon Core Wire, Ser. No. 08/812,140, entitled Pre-Stretched Catheter Balloon and Ser. No. 08/812,139, entitled Low Profile Catheter Value, all of which are hereby incorporated by reference in their entirety.

FIG. 3 illustrates another aspect of the catheter of the present invention. There is illustrated a guide wire 12 with an inflated occlusion balloon 25 extending from the distal end of a guiding catheter 11, also having an occlusion balloon 24 mounted thereon. As is typical with such guide catheters 11, a radiopaque marker ring 11A is indicated near the distal tip of the catheter 11. This allows the physician to detect the location of the catheter under fluoroscopy or other visualization. It is also typical in the construction of therapy catheters 13 (dashed lines) to provide a similar radiopaque marker 17 near the distal tip. For simplicity, FIG. 3 illustrates a hypothetical location of this therapy catheter marker 17, but illustrates the therapy catheter 13 itself in dashed lines. Again, the position of the therapy marker 17 is gauged by visualization means such as fluoroscopy.

With occlusion guidewires 12 of the type shown, however, the exact location of the occlusion balloon 25 is not always known. Moreover, the occlusion balloon 25 is typically relatively short so as to avoid interfering with the therapy in the treatment location. Thus, the guidewire 12 in which the occlusion balloon 25 is mounted may shift slightly during the procedure, and may interfere therewith or become damaged itself from the action of the therapy catheter 13.

In order to provide the physician with an ability to detect and rectify such movement, a series of radiopaque markers are formed on the body of the guidewire 12 as indicated in FIG. 3. These markers 22 are uniformly spaced apart by a given dimension such as 1 mm in order to also provide the physician with a reference system within the working area. In using these markers, once the relative positions of the guide catheter ring 11A and the therapy marker 17 are determined, the number of guidewire markers 22 in between these two reference points can be used to reposition the guidewire if necessary. Thus, any relative movement of any of these devices, i.e., the guide catheter 11, the therapy catheter 13, or the guidewire 12, can be detected and steered into the desired location in the patient's body as well as measured for easy correction.

Such markers 22 can be of a typical type and manufactured from radiopaque materials such as platinum, gold, etc. They can be embodied in the wall of the guidewire 12 or applied as plating to a reduced diameter portion thereof in order to maintain its smooth outer profile. Moreover, it should be noted that this feature of the invention can also be applied to other types of medical wires, with or without occlusion balloons, and in conjunction with other types of guiding or therapy catheters.

Non-linear Superelastic Nitinol

Figure 4A:
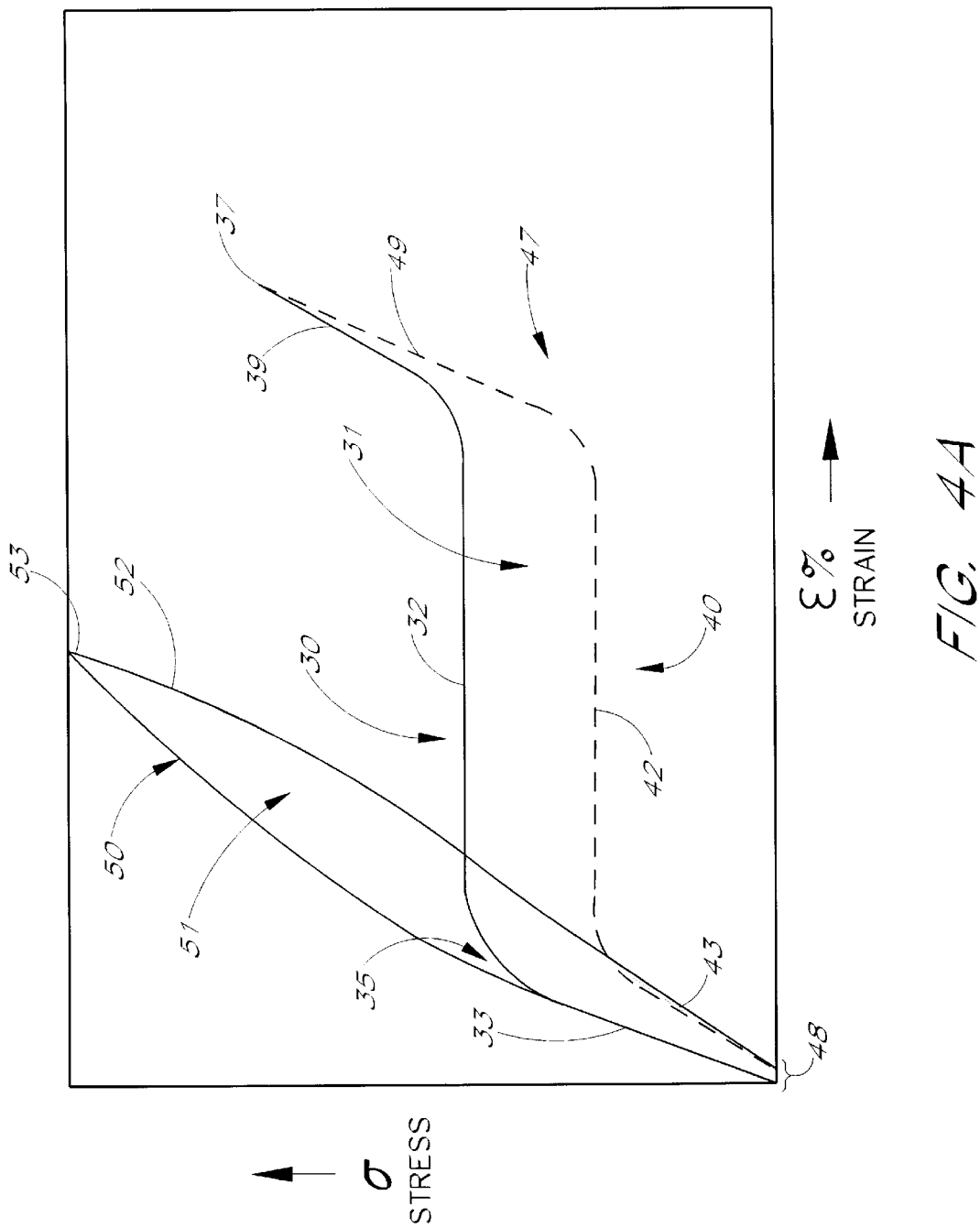
FIG. 4A is a graph comparing the stress-strain characteristics of non-transformational and transformational superelasticity.

In accordance with the principles of the present invention, the elongated body member 14 of the catheter 10 described above is advantageously constructed from a superelastic material which has been carefully selected and treated to provide unexpectedly excellent performance characteristics. In the preferred embodiment, the body 14 is constructed from a superelastic nitinol and, more particularly, a superelastic nitinol which exhibits non-linear behavior characteristics with respect to its stress-strain relationship (FIG. 4A). As a result, in addition to the catheter described above, many types of medical wires can be constructed to take advantage of these performance characteristics.

Although there are literally thousands of superelastic nitinol and stainless steel materials, their elasticity alone does not provide ideal performance in a medical wire. For example, there are many superelastic nitinol and stainless steel materials which, if formed into a medical wire, are too rigid or too limp to provide good performance characteristics, i e., their modulus of elasticity is either too high or too low, respectively. Thus, it has been discovered that there is a category of nitinol materials having structural and mechanical characteristics, besides superelasticity, which make them particularly suitable for medical wire applications. However, in order to fully appreciate these characteristics, a basic understanding of nickel titanium alloys and their construction is helpful.

Ni—Ti alloys or nitinol alloys are the most important of the shape memory alloys (SMA). Such materials can adjust their properties and shape according to changes in their environment, specifically changes in applied stress and temperature. In this respect, nitinol alloys can change their shape by strains greater than 8% and adjust constraining forces by a factor of 5 times. The scientific foundations of the shape memory effect is well known in the art.

Superelasticity refers to the ability of a material to reversibly transform its crystal structure and shape in order to relieve applied stresses so that the material can undergo large elastic deformations without the onset of plastic deformation. This superelasticity, often referred to as transformational superelasticity, exhibits itself as the parent crystal structure of the material as it transforms into a different crystal structure. In superelastic materials the parent crystal structure or the phase is known as the austenitic phase and the product crystal structure is known as the martensitic phase. Such formed martensite is termed stress induced martensite.

Figure 4B:
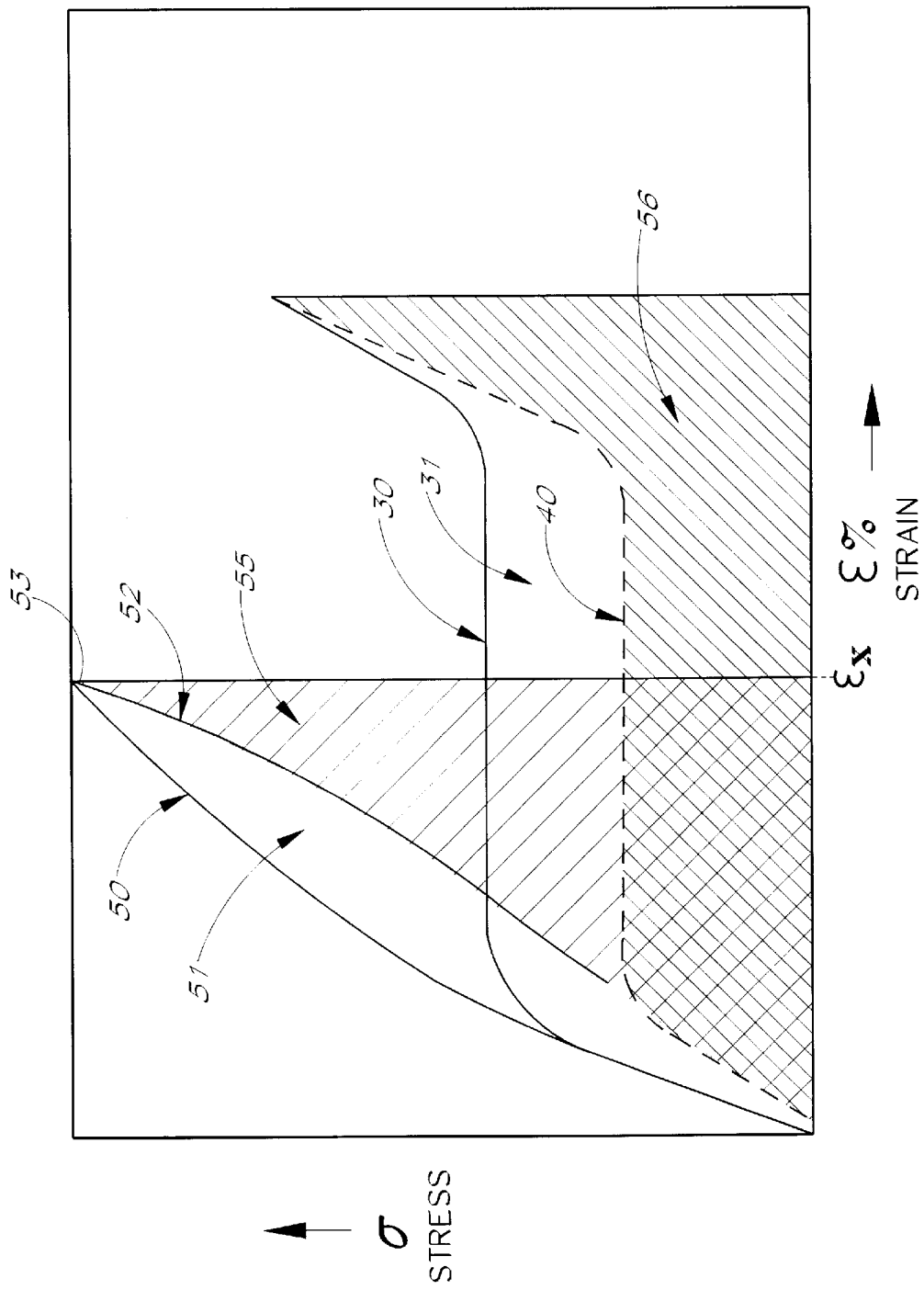
FIG. 4B is a graph comparing the stored deformation energies of non-transformational and transformational superelasticity.

As will be explained more fully hereinbelow, superelastic characteristics of the nitinol alloys can be best viewed by the stress strain diagrams obtained from various mechanical testing methods such as tensile tests, torsion tests, bending tests or compression tests. Among these methods, the tensile test emerges as the most common mechanical testing method. In particular, tensile tests provide very useful information about both the type of deformation and the amount of deformation that a test sample undergoes under an applied stress. In this respect, FIGS. 4A and 4B provide very valuable information about the deformation characteristics of the superelastic nitinol alloys under tensile test conditions. For the nitinol alloys, these tensile stress strain diagrams are equivalent to stress strain diagrams provided with torsion, bending and compression tests.

As shown in FIG. 4A, in a tensile stress-strain (deformation) diagram of austenitic superelastic alloys, superelastic materials in general exhibit two different types of non-linear elastic deformation characteristic. The first deformation characteristic, which is referred to as transformational non-linear superelastic deformation, can be depicted by a first hysteresis 31 defined by a loading curve 30 and an unloading curve 40. As is understood, the loading curve 30 and unloading curve 40 are non-linear curves thereby representing a non-linear superelastic deformation behavior. Similarly, FIG. 4A illustrates a second deformation characteristic referred to as non-transformational. Although sometimes referred to as "linear" superelastic deformation, non-transformational superelastic deformation is also non-linear due to a second hysteresis 51 defined by a loading curve 50 and an unloading curve 52. However, as will be explained more fully hereinbelow, the non-linearity in this case is a less emphasized non-linearity so that the curves 50 and 52 follow a rather smooth change. It is well-known in the art that the first and second hysteresis 31 and 51 occur due to internal friction and plastic deformation.

During transformational superelastic behavior, under the applied stress the curve 30 first follows a linear path 33 where the austenitic phase elastically deforms. The austenitic phase elastically deforms with increasing stress up to a critical yielding stress value 35 where martensitic transformation begins. After this critical stress point 35, the material continues to transform into martensite. Throughout the transformation, despite a constant increase in deformation rate of the material, the applied stress remains about the same critical stress value 35 thereby revealing the superelastic property of the material.

This is very important in the field of angioplasty since one can engineer a catheter apparatus to deliver a physiologically ideal stress and rely on the fact that this stress will be held constant throughout the angioplasty application. This superelastic behavior forms a loading plateau 32 on the curve 30 until the entire austenite phase transforms into the martensitic phase.

Still referring to FIG. 4A, at the end of the transformation, the curve 30 no longer follows a straight path but a linearly increasing path 39 where the martensitic material elastically deforms up to a point 37 where unloading begins. During the unloading, the martensite structure transforms into austenite structure. Due to internal friction, there is not an overlap of loading and unloading curves 30 and 40, and the unloading curve 40 moves down to lower stress values.

During the course of unloading, the martensitic phase is first unloaded along the linear portion 49 of the curve 40. At a critical stress value 47, martensite to austenite transformation begins and continues along the unloading plateau 42. Upon completion of austenitic transformation, the elastic deformation on austenitic material is unloaded along the linear portion 43. However, as is seen in FIG. 4A, the unloading does not totally reverse the superelastic deformation. In fact a permanent deformation or "set" 48 remains after the completion of unloading.

As also shown in FIG. 4A, in hysteresis 51, non-transformational superelastic deformation does not produce a plateau of constant stress. Due to little or no martensitic transformation, the loading and unloading curves 50 and 52 demonstrate a less non-linear increase and decrease respectively. In other words, changes in superelastic deformation behavior are not as drastic as in the case of transformational superelasticity. In fact, as is seen in FIG. 4A, curves 50 and 52 adopt a rather smooth change in non-linearity. In such materials, a high level of elastic deformation can only be possible with the application of high levels of stress. However, it is understood that the modulus of elasticity for such non-transformational nitinol alloys is still significantly lower than the modulus of elasticity for stainless steels.

The difference in elastic deformation behavior for the transformational and non-transformational cases can be clearly seen in FIG. 4B by means of stored elastic energies for each deformation case. The stored elastic deformation energy can be defined with areas 55 and 56 under the respective unloading curves 40 and 52. It would be understood that, at a random deformation value $\epsilon_x$, the non-transformational superelastic deformation stores more elastic deformation energy which is equivalent to spring back energy of the superelastic material. The spring back energy in transformational case can be increased by increasing the deformation range beyond $\epsilon_x$. However, an increase more than 6% deformation reduces the stiffness of the material and hence reduces the spring back force and the unloading stress.

Medical Wires

The medical wires of the present invention take advantage of particular non-linear superelastic nitinol characteristics to achieve better functional performance, especially in terms of flexibility and handleability. In addition, because of their ability to withstand permanent deformation, the present medical wires also demonstrate, in practice and under adverse conditions, improved characteristics of pushability, trackability, and torqueability, especially in comparison to previous superelastic and elastic wires. Thus, in addition to its superelasticity, the present medical wire also exhibits the following excellent characteristics: very high recoverable strain with virtually no permanent set; a relatively low modulus compared to other elastic materials; and some hysteresis in its unloading curve.

As noted above, superelasticity refers to the ability of a material to recover strain after deformation. However, under adverse medical conditions, such recovery is not only inhibited, but is very important in order to avoid injurious effects on the patient. The medical wire of the present invention advantageously recovers strain over a wide range of deformations, typically 1–8% and even 9–10% in some cases where there has been careful attention to the heat treatment of the wire material. This high recoverable strain characteristic in the present wire allows the wire to traverse a wide range of tortuous turns without plastic deformation, which of course would inhibit or destroy the performance of a wire.

Figure 5A:
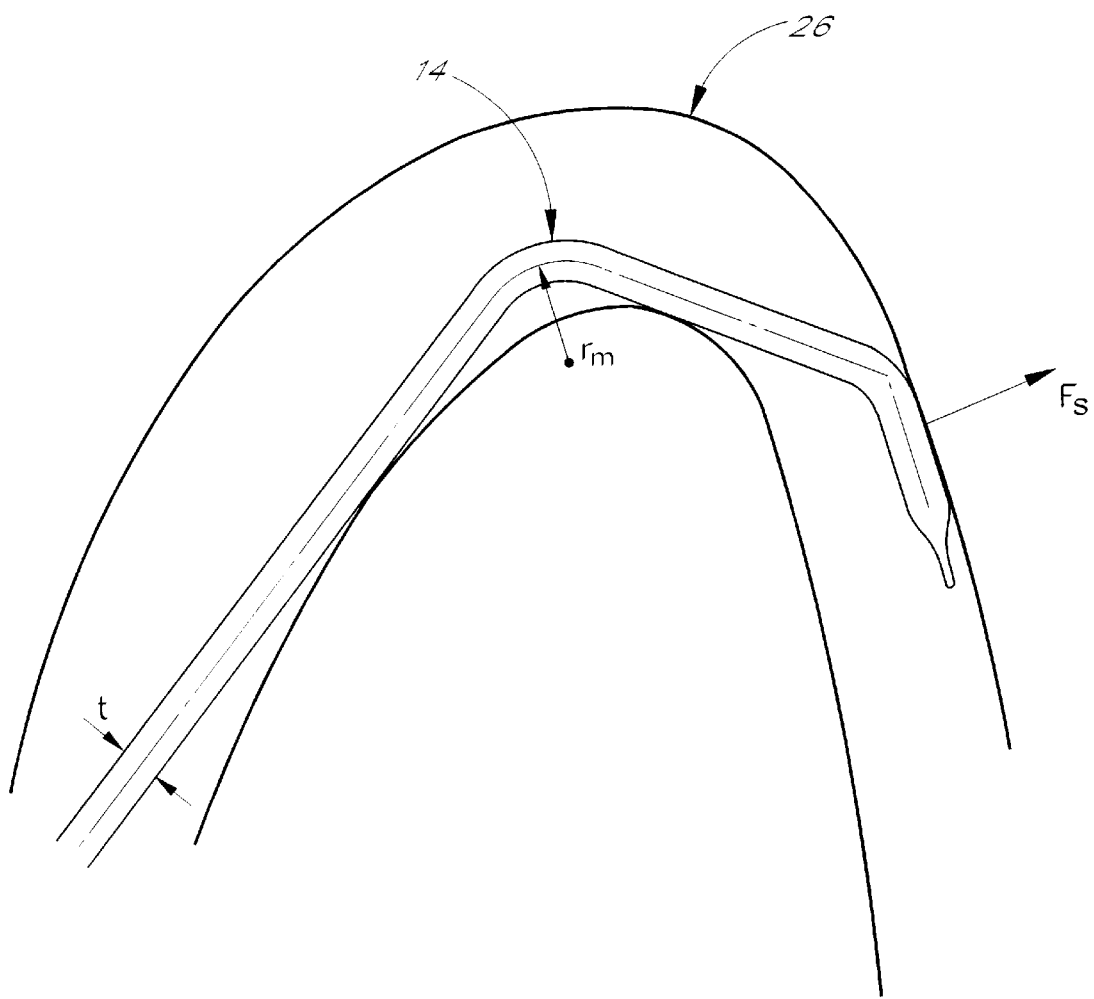
FIG. 5A is a schematic cutaway view of a vessel and a medical wire positioned within the vessel.

This characteristic can be illustrated schematically with reference to FIG. 5A. This figure is a cutaway view of a vessel 26 exhibiting a sharp turn. The medical wire is shown traversing the turn; although, it will be noted that no guide catheter within the vessel 26 is illustrated for simplicity, and that the medical wire 14 of the present invention may be used with or without a guide catheter. With the medical wire 14 of the present invention, it has unexpectedly been discovered that turns of even very small radii can be traversed with confidence without plastic deformation. The following calculations adequately illustrate this point. That is, for a hollow tube, the strain experienced in bending is given as follows:

$$\varepsilon = \frac{t}{2r_m}$$

where:
 $\epsilon$=recoverable strain (%)
 t=diameter of the hypotube
 $r_m$=mean radius of the bend in the tube In this case, the radius of the bend is that which is illustrated in FIG. 5A and is the degree of bending that the tube can suffer without plastic deformation. Since the maximum recoverable strain is usually known, the equation can be easily solved for the mean radius ($r_m$) of the smallest bend possible without plastic deformation, which is as follows:

$$r_m = \frac{t}{2\varepsilon}$$

For an elastic material, such as stainless steel, a typical recoverable strain for a hollow medical wire can be as high as 0.4%. If the medical tube has a diameter of 0.014" (overage), then the radius is 1.75". This means that an elastic stainless steel wire having this maximum strain cannot bend around a turn having a radius smaller than 1.75" without suffering plastic deformation. However, for the medical wire 14 of the present invention, having similar dimensions, maximum recoverable strain can easily be about 6%. Thus, solving the above equation for the radius yields a result of only 0.117". For maximum recoverable strains of 8%, which are within the range of the present invention, even tighter turns can be traversed.

Thus, it should be observed that the medical wire 14 of the present invention can successfully avoid permanent deformation over a wide variety of adverse conditions, thus providing excellent tortuosity characteristics. Furthermore, because plastic deformation is avoided, the pushability and torqueability characteristics of the present wire 14 are maintained. This is compared with previous medical wires which begin with as good or even better characteristics of pushability and torqueability, but because they experience plastic deformation traversing a certain number of tortuous turns or pushing against obstructions, their performance characteristics in actuality are greatly diminished.

This point can be illustrated in greater detail with the following discussion. Nitinol, in general, is used in certain medical wire applications because of its enhanced flexibility and corresponding kink resistance in comparison with stainless steel. Kinking greatly reduces the ability to push or steer a wire into the desired location, and also obviously reduces the ability to slide a catheter over the wire. Thus, the flexibility of nitinol, which derives generally from its low modulus, is an advantage in certain applications. Stainless steel, however, according to conventional thought, is more often selected for medical wire and catheter applications due to its enhanced torqueability and pushability characteristics. These characteristics are derived from the greater rigidity of stainless as compared to nitinol. From this perspective, therefore, the flexibility of nitinol can be considered a disadvantage, and indeed, many nitinol alloys are too flexible to perform well in connection with torqueability and pushability.

It can be demonstrated, on the other hand, that nitinol alloys which are carefully selected in accordance with the principles of the present invention can out perform stainless steel not only in terms of flexibility, but of torqueability and pushability as well. This is true for a wide range of recoverable strains, including, but not limited to those within the elastic limit of stainless steel (being about 0.4 to 0.6% in tension). It is especially true for strains beyond the elastic limit of stainless steel. It will be noted that, in bending, the elastic limit of a solid stainless steel wire may be slightly higher than the range quoted above (such as about 0.8%); although, in a tubular construction (e.g., a hypotube), the elastic limit of stainless may vary. Nevertheless, it has been demonstrated that the hollow medical wires and catheters of the present invention, constructed in accordance with the material selection criteria prescribed herein, provide excellent torqueability and pushability characteristics, as well as flexibility and kink resistance. Moreover, as an important aspect of the present invention, because the forces necessary to torque and to push the present nitinol wires and catheters are greatly reduced as compared to stainless steel, the present invention also demonstrates enhanced characteristics of handleability.

Thus, it has been demonstrated in torqueability tests that, under bending strain and in conditions of low wall friction, nitinol wires within the scope of the present invention come much closer to the ideal 1:1 than stainless steel wires of similar diameter. The wall friction, illustrated in FIGS. 5A and 5B, relates to the containment of the wire as it undergoes bending. Under conditions of higher wall friction, the nitinol wire again out-performed the stainless steel wire, even below the elastic limit of the stainless steel. This is probably due to the higher coefficient of friction and higher modulus of the stainless, which causes it to form local indentations in the wall of the tubing (which may take the form of a guide catheter or the wall of a blood vessel). Thus, the stainless steel wire tends to lock in place where it pushes against the containment wall, resulting in greater resistance to torquing. Under actual conditions, this can result in damage to a guide catheter or, more seriously, the wall of a blood vessel. Thus, nitinol wires within the scope of the present invention not only provide enhanced torqueability, but also help to avoid damage to sensitive tissue.

Likewise, it has been demonstrated that the forces to achieve torque in a nitinol wire are approximately five times less than those of stainless steel wires, both within and beyond the bending elastic limit of the stainless. This low force requirement makes the nitinol wire much easier to manipulate and provides greater handleability and "feel" for the physician.

With respect to pushability, likewise the forces for nitinol wires as compared to stainless are several times less, particularly beyond the elastic limit of the stainless undergoing bending strain. Overall, as noted above, the nitinol wires and catheters of the present invention provide enhanced characteristics over similar sized stainless wires and catheters not only in terms of flexibility, but also torqueability, pushability, and handleability.

In addition to the advantages of unexpectedly high recoverable strain, the medical wire of the present invention is also able to achieve other advantages by exhibiting a relatively low modulus. That is, for a given strain, the stress exhibited by the present medical wire 14 is relatively lower than with previous superelastic medical wires. This characteristic advantageously exhibits itself in the functionality of the present wire 14. For example, in the context of a tortuous path, as the wire 14 turns the corner of a tight radius turn, it becomes "loaded" in the sense that the bending it experiences causes a certain amount of deformation or strain. According to this stress-strain relationship, there is induced a corresponding stress force in the wire 14, which manifests itself in the tendency of the material to want to straighten out to its original straight configuration. In the medical procedures of the type in which the present wire is utilized, this can be a dangerous situation. As illustrated in FIG. 5A, the bent portion of the wire pushes against the wall of the vessel 26 with a particular force $F_s$, (or in the case of a guide catheter, the wire pushes against the guide catheter which in turn contacts the wall of the vessel 26). With higher modulus materials, this force may be great enough to cause damage to the vessel 26. However, with the present wire 14, even over a wide range of recoverable strains, this force is minimal.

Figure 5B:
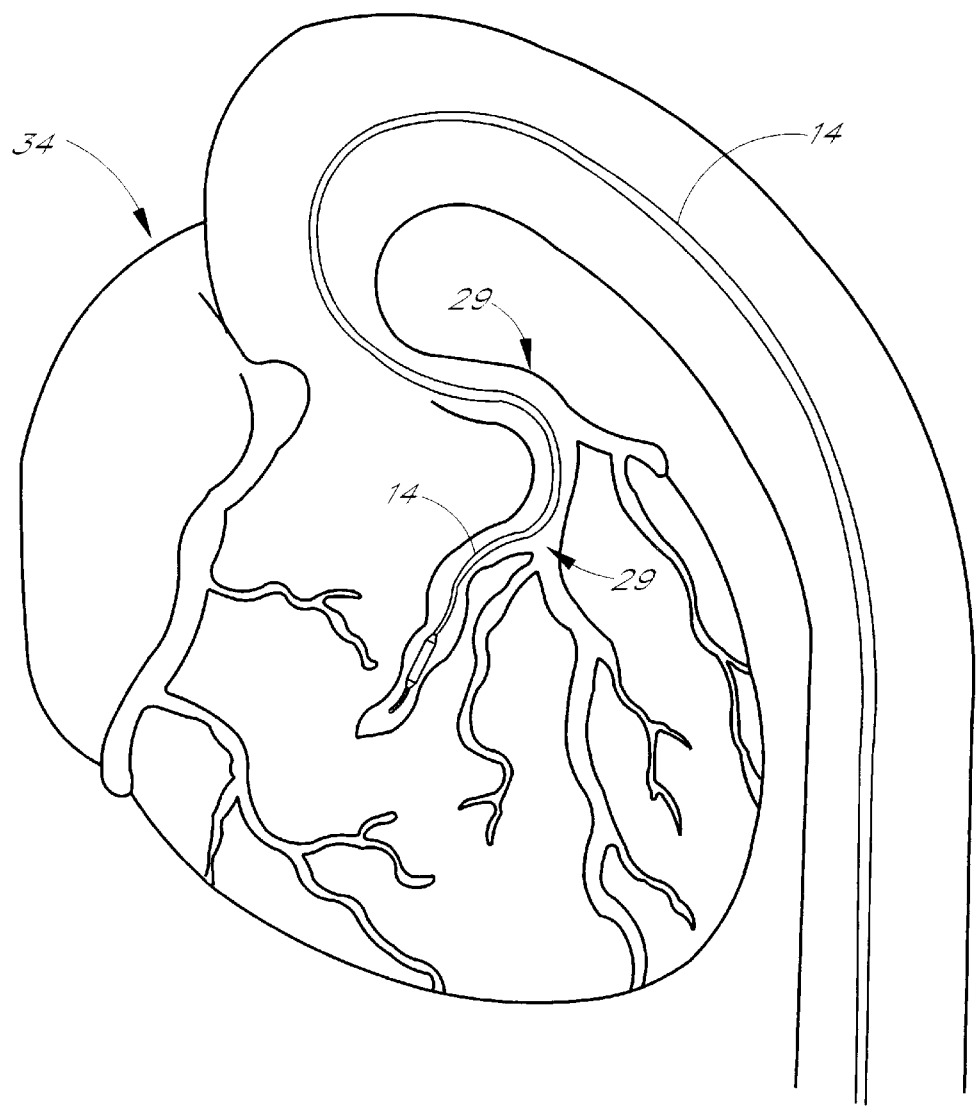
FIG. 5B is a schematic view of a medical wire positioned within the coronary arteries.

Perhaps an even more important advantage of these low modulus characteristics is the reduced frictional forces experienced by the wire as it courses through the vasculature of the patient. Because the frictional force is proportional to force and the area of contact against the wall of the vessel or guide catheter, such frictional forces are proportionally reduced as the force is reduced. Thus, the pushability and handleability of the present wire 14 are excellent. These characteristics can be best demonstrated by the example illustration in FIG. 5B. FIG. 5B shows the guide wire 14 of the present invention within a coronary artery 29 in the heart 34. Smooth and consistent pushing forces provide a better feel of the wire for the physician, and can be utilized to precisely traverse the vasculature of the patient and position the wire at the precise location for successful treatment.

Although stress values can be advantageously adjusted according to heat treatment or other post-construction condition, stress values in the range of 20–100 (Klbs. per square inch) (ksi) (150 MPa–750 MPa) have been found to be suitable for the present medical wire, at least at strains in the range of 2–6% or more.

Another advantageous characteristic of the present medical wire is its ability to generate an even lower stress upon unloading. That is, in contrast to the above discussion directed to low stress values upon loading (i.e., as the wire traverses a tight turn), the present wire exhibits even lower stress values as the wire completes the turn (i.e., during unloading). As soon as a length of the wire is sufficiently beyond a turn to allow it to straighten itself, it may be considered unloaded. Thus, the unloading portion of the stress strain curve in the present wire gives, for a given strain, the stress value induced in the material as it recovers its strain. As noted above, because of the hysteresis or the non-linearity of the present superelastic nitinol, unloading stress will be even less than that of the loading stress. Thus, the area under the unloading curve is sometimes referred to as the elastic or springback energy because it characterizes the forces experienced by the material as it returns to its original configuration. However, a high springback energy causes a whipping effect at the distal end. Thus, these lower unloading stresses contribute to the smooth handleability of the present wire.

These advantages of the present medical wire, which derive from the non-linear superelastic behavior of the particular nitinol alloys used therein, may be achieved through heat treating (annealing). However, although other condition methods can be utilized to achieve the present advantages, where careful attention is paid to the heat treatment of the wire, it can reach a unique stage of non-linear superelastic nitinol referred to as "transformational." This is because the material actually undergoes a phase transformation during loading and unloading, as explained above. Such transformational superelastic nitinol provide additional advantages in connection with the medical wire of the present invention. For example, they exhibit a substantially higher recoverable strain in the range of 8–9%, as compared to 4–5% maximum recoverable strains with non-transformational nitinols. As explained in detail above, these higher recoverable strains achievable from the transformational material provides many functional advantages.

In addition, the corresponding stress levels of such transformational nitinols are in the range of 200–500 MPa. Under loaded conditions, the plateau stresses are preferably in the range of 300–500 MPa, while upon unloading the stresses are less, e.g. 80–400 MPa. Furthermore, the hysteresis of the unloading curve increases with greater deformation; thus, at about 7% strain, an unloading stress of about 200 MPa is preferred.

Moreover, an even lower modulus is achievable with such transformational nitinols. In fact, as noted above and illustrated in FIGS. 4A and 4B, one of the distinguishable characteristics of such materials is a relatively constant loading stress which is typically referred to as a "loading plateau." That is, over a wide range of recoverable strains, the material exhibits a substantially constant stress value. As explained above, this allows the material to exhibit excellent performance characteristics, in terms of low friction and handleability. In use, doctors are able to apply smooth, constant pushing forces without a concern for excessive forces needed to traverse tight turns.

Thus, an important aspect of the present invention is the selection of the proper non-linear superelastic nitinol sufficient to achieve the desired functional characteristics which are desired for a particular application. It should be noted that the selection of the appropriate non-linear material may vary depending on such desired characteristics and the various design tradeoffs which must be made. Thus, in a given application, a transformational non-linear nitinol may be selected versus a non-transformational type. That is, in an application where cyclical deformations are experienced, the resistance to fatigue-induced plastic deformations is an important functional characteristic. Thus, one may select a non-transformational type non-linear nitinol because of its narrower hysteresis and higher strength. On the other hand, where the material must undergo many cycles (about more than 100 cycles) better fatigue-resistant characteristics can be achieved with the transformational nitinols.

Likewise, as discussed below in more detail, a given medical wire may also be constructed so as to have characteristics of both transformational and non-transformational materials. For example, the proximal end of the medical wire may be constructed from a non-transformational nitinol to provide enhanced pushability and trackability characteristics, while the distal end of the same wire (say, in the range of the distal 2 to 15 cm) undergoes special conditioning in order to achieve a transformational state. Thus, the distal end will be softer and will exhibit the constant, reduced stress forces at even very high recoverable strains which are characteristic of non-transformational nitinols. Other advantages can be achieved with composite wires constructed from non-linear nitinols and stainless steel or other materials.

In the case of hollow medical hypotubes, special problems must be overcome. First, the trackability of the wire will be a challenge due to the reduced body mass. Thus, it is preferable to select materials with a higher loading plateau stress than solid wire. Secondly, the frictional characteristics of tubing will have to be addressed by applying friction reducing treatments. Third, the ductility of hypotubes must be addressed. Because of the reduced wall thickness, failure of the material is a risk. Greater resistance to failure can be achieved by heat treating at higher temperatures and less cold work. Finally, surface defects must be avoided because stress tends to localize at such nicks or indentations (it being recognized that such defects represent a large percentage of the surface wall thickness). Thus, careful inspection and selection of materials must be exercised such that the hypotube has defects of 15 microns or less.

As merely one example of a suitable non-linear superelastic nitinol, the catheter illustrated in FIGS. 1–2 can be constructed, at least in part, from a transformational non-linear nitinol having a recoverable strain of about 8%. However, maximal elongation and failure is at least about 14%, providing strong safety characteristics. Because of the material's transformation, it exhibits a loaded plateau stress at room temperature of about 75 ksi (500 MPa) and an unloading plateau stress of about 25 ksi (170 MPa).

In regard to material selection, it will be noted that the process of alloying, nickel and titanium is a well-established art for the production of nitinol; however, as noted above, there are many nitinol materials which may not supply the desired performance characteristics. Nevertheless, various types of nitinol materials which may be successfully used in the construction of the medical wires of the present invention are commercially available from companies such as Memory Corp. which provides one suitable nitinol material known as Tinel® Alloy BB.

Superelasticity in Ni—Ti alloys also depends on temperature. Martensitic or austenitic transformations start and finish at certain temperature ranges. Thermal or mechanical treatments in the history of the material may change these temperature ranges. In this respect Ms-temperature refers to temperature that martensitic transformation from austenite begins. At the Mf-temperature martensitic transformation finishes. Further, temperatures As and Af indicate the respective beginning and the end of austenitic reversion. However, as indicated before, the applied stress shifts these temperature ranges. In case of stress induced martensitic transformation, Md temperature is defined as the temperature above which stress-induced martensitic transformation cannot occur. It is understood by those skilled in the art, that superelastic properties can be observed at temperatures above Af and below Md. In fact fully superelastic effects are found over an even narrower range, typically only 10–40° C. in width.

Thus, for a given superelastic nitinol at room temperature, it will be noted that, at body temperature, the stress roughly increases according to the equation:

$$\Delta\sigma \approx 6 \times \Delta T$$

where $\Delta T$ is the temperature difference between the body and the room temperatures. $\Delta\sigma$ is the amount of added stress due to the increase in temperature. For purposes of the present discussion, the superelasticity of nitinol is considered to be its state during use more or less at body temperature.

Figure 6:
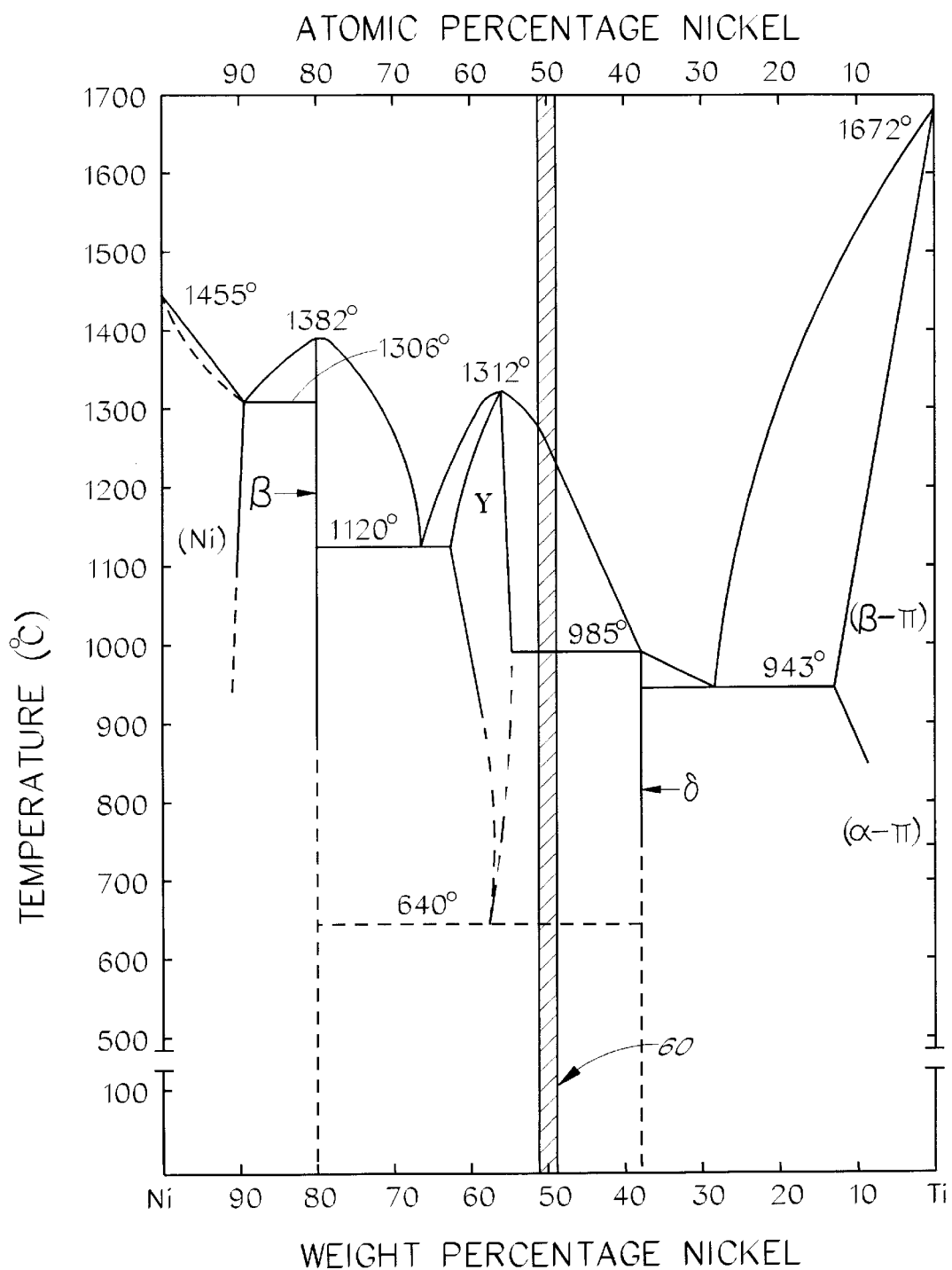
FIG. 6 is a Ni—Ti phase diagram.

The alloy composition range 60 of the superelastic Ni—Ti alloy of the present invention is shown graphically in the Ni—Ti binary phase diagram in FIG. 6. Binary phase diagrams are composition-temperature diagrams which provide valuable information for specific alloy compositions, such as the formation of various equilibrium phases of these alloy compositions and their respective temperature ranges. In the preferred embodiment, Ni—Ti alloy composition is preferably selected from a Nickel rich composition ranging from 50.0 atomic % Ni to 51.5 atomic % Ni, preferably from 50.6 atomic % Ni to 50.9 atomic % Ni. However, in accordance with the principles of the present invention, the superelastic alloy of the present invention may be selected from the group of nitinol family ternary alloys including Ni—Ti—V, Ni—Ti—Fe, Ni—Ti—Cu, Ni—Ti—Co, Ni—Ti—Cr, Ni—Ti—Nb, Ni—Ti—Pd or non-nitinol Fe—Mn—Si ternary alloys. For the nitinol family ternary alloys, a preferred composition range basically determined by the formula:

$$\text{Ni(Atomic \%)} + \text{Ti(Atomic \%)} + 3^{rd}\text{ Element(Atomic \%)} = 100$$

where, $3^{rd}$ Element(Atomic %) is less than 14% atomic weight. The $3^{rd}$ Element defines V, Fe, Cu, Co, Cr, Pd and Nb elements of the ternary compositions, such as Ni—Ti—V, etc.

Distal Section

The distal section 14B (FIG. 1) of the nitinol hypotube 14 must be very flexible to facilitate the entry of the distal section 14B into a desired blood vessel during angioplasty procedures. This is especially true of the distal most 30 cm or so of the medical wire which, in the case of a coronary guidewire, must enter the vessel without the protection of a guide catheter. Therefore, this section must exhibit a high degree of softness and a very low modulus. In accordance with the principles of present invention, this flexibility can be provided in various ways such as reducing the thickness at distal-end 14B or applying appropriate heat-treatments to the distal-end 14B, or both. Within the scope of this invention, it will be understood that the term heat treatment refers to any thermal treatment that has been applied to the material before or after inserting into patient's body.

In one embodiment, the wall thickness of the distal portion 14B of the hypotube 14 can be reduced to accommodate the need for flexibility at the distal end 14B. Thus, for example, the wall thickness can be reduced to about 0.001 to about 0.0015". Thickness reduction at the distal-end 14B can be done by either tapering the distal-end or performing a uniform thickness reduction along the distal-end 14B. Preferably, the distal-end 14B of the hypotube 14 can be tapered to a lower diameter to provide distal flexibility and proximal stiffness.

In another embodiment, the distal-end may be heat treated for a period of time to provide flexibility and softness. The heat-treatment reduces the force required to reach the elastic plateau 32 (FIG. 4A) so that the heat treated distal-end 14B is more flexible than the proximal-end. The heat treatment can be done in salt baths such as the salt baths containing potassium nitrates, and preferably at a temperature range between 300 and 600° C., and for a preferred time range of 10 to 60 minutes. It should also be noted that other sections of the medical wire, besides the distal section, could also receive special heat treatments in order to vary their characteristics for a particular purpose.

Manufacturing Process

In the manufacturing of the preferred embodiment, the alloy of the present invention can be made superelastic by facilitating various thermal and/or mechanical treatments. The alloy can typically be shaped into the hypotube 14 or core wire 20 by cold working the material and/or heat treating the alloy. In the case of the hypotubing 14, the cold work can be performed by reducing the tube wall diameter or the outer diameter of the tube. Various facilitating instruments such as swager, metal extrusion and drawing equipment can be utilized to provide cold work. In the preferred embodiment, the hypotube 14 is shaped by cold working the material at a preferred cold work range of 20–40%. In the general manufacturing process, Ni—Ti tubes are typically manufactured by inserting a core element in a cylindrical Ni—Ti bar and drawing this bar into smaller diameters through the use of series of dies and intermediate heat treatments above 600° C.

Following the cold work, the hypotube is preferably heat treated at a temperature range between 500 and 600° C. This heat treatment can preferably be done in a salt bath, such as potassium nitrate, or in a protective atmosphere, such as Argon gas, for 10 seconds to 60 minutes. In this embodiment, the heat treated hypotube 14 may not be quenched but preferably cooled down to room temperature in a protective atmosphere. In the preferred embodiment, the resulting superelastic hypotube has a martensitic transformation temperature (Ms) of −30° C., and an austenitic transformation temperature (As) of 11° C. The stress level at loading plateau 32 (FIG. 4A) or loading plateau stress is 450 MPa, and the stress at unloading plateau 42 is 150 MPa. Under these conditions the material presents more than 6% superelasticity.

In another embodiment, the heat treatment can be performed at less than 500° C. This material can also have more than 6% superelasticity. However, the heat treatment temperature causes a significant shift in stress and transformation temperatures, Ms and As respectively. Particularly, lower heat treatment temperature increases the plateau stress. In this embodiment, the resulting material have a loading plateau stress of 550 MPa and an unloading plateau stress of 320 MPa. In this respect, Ms temperature is −75° C. and As temperature is −3° C.

Figure 7A:
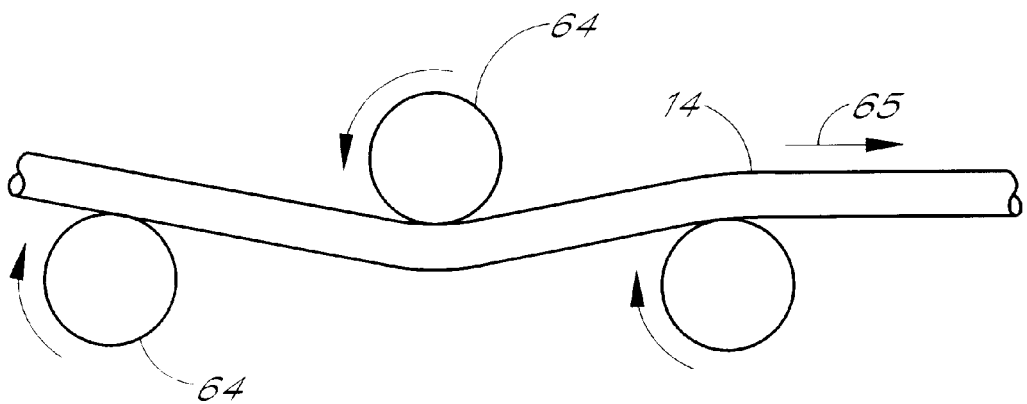
FIG. 7A is a schematic view of an embodiment to straighten the hypotube by rolling.
Figure 7B:
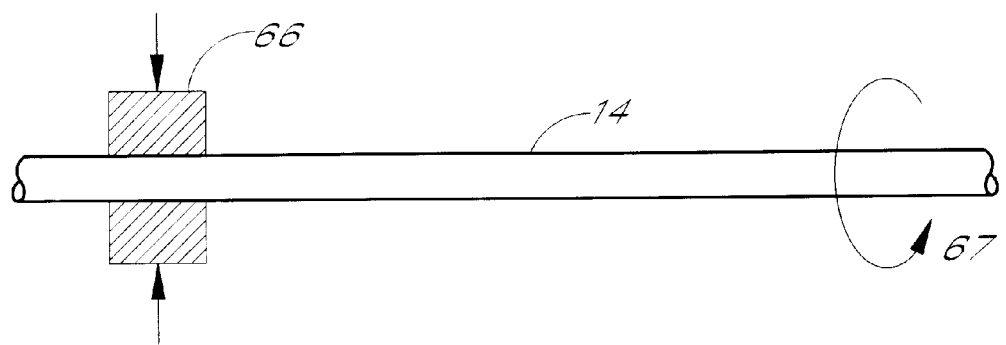
FIG. 7B is a schematic view of an alternative embodiment to straighten the hypotube by twisting.

During the manufacturing of hypotube 14, the roundness and the straightness of the hypotube present an important problem. It is well-known that many cardiovascular applications require the use of straight and round tubing This can be done through a series of thermo-mechanical treatments following the production of hypotube by the method given above. Thermo-mechanical treatments include twisting, pulling and bendings combined with heat treatments above 300° C. Various facilitating instruments can be used to provide roundness. As illustrated in FIG. 7A, the hypotube 14 of the present invention can be drawn (in the direction of arrow 65) among a series of rotating rollers 64 to provide required roundness. Similarly, as illustrated in FIG. 7B, the body of the hypotube 14 can be twisted about the longitudinal axis of the hypotube to provide further roundness. Twisting can be performed continuously or in discrete process steps. Twisting may be performed by securing the one end of the hypotube 14 using suitable means 66, and rotating the other end in the direction of the arrow 67 as in the manner shown in FIG. 7B. During the twisting, variations in tube wall thickness are uniformly distributed along the length of the tube. However, it will be appreciated that twisting methods are well-known in the art and may be performed in a variety of ways.

In another embodiment, following the cold work, a solution treatment above 500° C. and an aging process at relatively low temperatures, preferably 400° C., may be applied to the cold worked hypotube. In such solution treated and aged structure, the resulting material has a loading plateau stress of 300 MPa, unloading plateau stress of 100 MPa. This process also presents more than 6% recoverable strain.

In another embodiment, the material may only be cold worked and the cold working process is not followed by an annealing step. In this embodiment, the material superelasticity follows the hysteresis 51 as shown in FIG. 4A. There are no plateau stresses or defmite transformation temperatures. This material exhibits about 4% superelasticity.

The hypotube 14 is preferably coated with an outer lubricous material coating, such as Teflon, to increase the lubricity of the hypotube 14. The process of Teflon coating requires temperatures above 200° C. However, such high temperatures may interfere with the previous heat treatments and cause unwanted property changes, such as over softening of the material. In order to prevent such drawbacks, it is preferred that the Teflon coating be performed during some of the final heat treatments of the hypotube 14 so that the properties of the hypotube remains unchanged.

Composite Wires and Methods of Construction

In manufacturing of the catheter apparatus 10, it may be constructed using a single nitinol hypotubing or a composite structure comprising various tubing materials such as stainless steel, tantalum, titanium or nitinol alloys with varying Ni contents or even plastics.

Figure 8A:
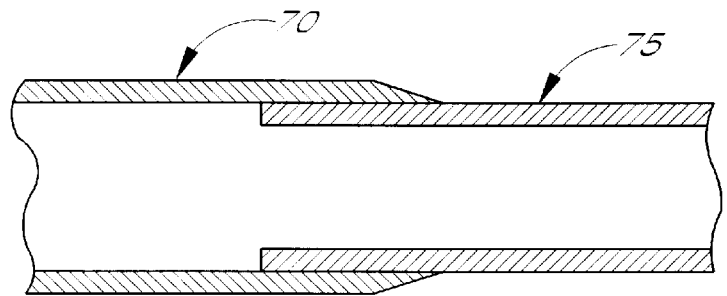
FIG. 8A is a schematic cross-sectional view of an embodiment of a composite hollow guidewire.

As illustrated in FIG. 8A, an exemplary composite structure can be formed by attaching a stainless steel hypotube 70 to a Ni—Ti hypotube 75 by using suitable adhesives, soldering, brazing, or press fitting, as in the manner shown in FIG. 8A. In this embodiment, Ni—Ti hypotube 75 may form the distal portion of the catheter apparatus 10 and have a length of about 20 cm. However, it will be noted that the composite wires of the present invention may also include other sections, beside the distal section, comprised of non-linear nitinol. Thus, in this regard, the present composite medical wire will have two or more effective moduli in order to provide greater versatility in performance.

Figure 8B:
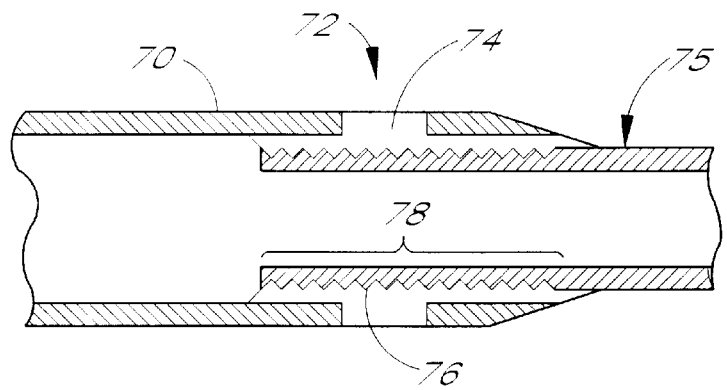
FIG. 8B is a schematic cross-sectional view of a joint in the composite hollow guidewire.

Another method of joinder is illustrated in FIG. 8B. A portion 78 of the proximal end of the nitinol hypotube 75 is fitted into the distal end of the stainless steel tube 70 and a joint 74 can be formed as in the manner shown in FIG. 8B. The joint material, such as solder or adhesives, can be applied through one or more holes 72 that are previously formed at the distal end of the stainless steel tubing 70. Additionally, in order to provide a better adhesion between the joint material and the nitinol hypotube, the outer surface of the fitting end 78 of the hypotube may be modified as shown, or in other ways. Alternatively, crimping or press fitting may be also applied to join materials.

Figure 8C:
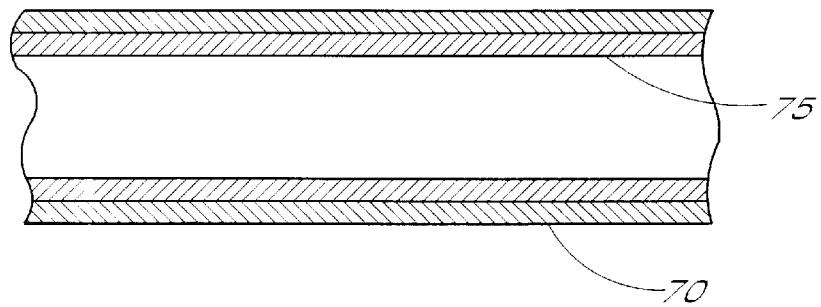
FIG. 8C is a schematic cross sectional view of another embodiment of the composite hollow guidewire.

As illustrated in FIG. 8C, in an alternate embodiment, the stainless steel hypotube 75 may be disposed concentrically about the Ni—Ti hypotube 70. In this embodiment, the stainless steel hypotube is sealingly secured about the periphery of the Ni—Ti hypotube 75 by using suitable adhesives.

In some cases, the component sections of the composite wire may have equal or approximately equal diameters. In other cases, one section may have a diameter greater than the other. For example, in order to avoid a problem known as "scooping", a composite guidewire may be constructed so as to have a proximal section OD of 0.035" or 0.018" (to allow certain therapy devices to ride thereover more efficiently) and a distal section of 0.014" (to provide a narrow profile to cross the lesion).

Irrigation Catheters

The hollow guidewire of the present invention can be advantageously used to deliver fluids for specific medical applications including coronary and neurological applications. During the course of such applications, it is often essential to deliver fluids to specific locations within the body. This fluid delivery is carried out using irrigation catheters. Particularly, irrigation catheters serve as passage ways for delivery of fluids comprising either a contrast media to permit X-ray detection or other media to achieve localized drug therapy. However, if there is a balloon incorporated at the distal end this fluid may also comprise a fluid, such as saline, to inflate the balloon.

In prior applications, typical fluid delivery procedure incorporates the use of a guidewire in combination with the use of an irrigation catheter. In this type of combination system, the irrigation catheter simply rides over the guidewire to reach the desired body location. The diameter of this combination system is significantly larger than the external diameter of the guidewire itself. Therefore, such systems are bulky and have limited applications for especially narrow and tortuous vessels such as vessels within the brain.

As illustrated in FIGS. 9A–9C, irrigation catheters constructed from the present invention overcome these limitations by providing a nitinol hollow guide wire having the capability to pass fluid therethrough. FIG. 9A illustrates a preferred embodiment of an irrigation catheter 80A constructed from superelastic nitinol hollow wire of the present invention. In this embodiment, the irrigation catheter 80A is comprised of an hypotube 81 and a coil member 82. The hypotube 81 is provided with proximal and distal ends 81A and 81B and as well as a lumen 84 extending along the hypotube 81 and thereby providing a fluid passage way. The coil member 82 of the catheter 80A is joined to the distal end 81B of the hypotube 81 as in the manner shown in FIG. 9A. The distal end 81B of the hypotube 81 may also include one or more perforations 85 thereof so that fluids can be delivered into or received from the desired body locations. In addition to distal perforations 85, gaps between the coil turns 86 also provide an effective passage way to deliver or receive fluids through coil member 82. Therefore, in this embodiment, perforations 85 at the distal end 81 A of the hypotube 81 are optional so that the fluid may exit or enter the catheter 80A from the coil member 82. Although the catheter 80A of the present invention can be used for delivering drugs to the distal body locations, the catheter 80A can also be used in those applications where irrigation and aspiration are necessary for emboli removal. For the most available cardiovascular catheters, the outer diameter of this irrigation catheter must be 0.38" or smaller.

FIG. 9B shows a second embodiment of the present invention which comprises a multilumen irrigation catheter 80B. In this embodiment, a portion of the catheter 80B comprising the hypotube 81 and the coil member 82 is configured similar to that of first embodiment. As a departure from the previous embodiment, however, the present embodiment also comprises a balloon member 88 and a conduit 90. The conduit 90 is preferably disposed along the inner lumen 84 of the hypotube 81. The balloon member 88 is coaxially mounted on the distal end 81B of the hypotube 81 as in the manner shown in FIG. 9B. The conduit 90 is provided with distal and proximal ends 90A and 90B as well as an inner lumen 91.

In this embodiment, the proximal end 90A of the conduit is preferably connected to a gas source (not shown), while the distal end 90B is connected to the balloon member 88 through an inlet port 92 in the distal end 81B of the hypotube 80. The distal end 90B of the conduit 90 and the inlet port 92 are sealably connected to each other by suitable means such as adhesive to avoid any gas leak. In this arrangement, the inner lumen 91 of the conduit 90 connects the gas source to the balloon member 88 so that the gas from the gas source can inflate the balloon member 88.

The conduit 90 is preferably made of a flexible material such as polymide, polyamide, or the like alloy and is in the form of hypotubing. Preferably, the outer diameter of the conduit 90 is significantly smaller than the inner diameter of the lumen 84 of the hypotube 81 so that fluid in the lumen 84 can flow without any restriction. In this embodiment, carbon dioxide ($CO_2$) gas is preferably employed to inflate balloon member 88. In fact, ($CO_2$) gas easily dissolves in blood and does not cause any harm in the patient's body, if an accidental leak occurs. If desired, however, the balloon member may be inflated using any of a number of harmless gases or fluids, or possible combinations thereof. In applications, the irrigation catheter 80B may function as the catheter 80A in the first embodiment. However, with the inflatable balloon member 88, the catheter 80B can be advantageously used for occlusion and irrigation therapies.

FIG. 9C shows a third embodiment of the present invention which comprises another single lumen catheter 80C as in the case of first embodiment. In this embodiment, a portion of the catheter 80C comprising the hypotube 81 and the coil member 82 is also configured similar to that of first embodiment. The present embodiment also comprises a balloon member 88. The balloon member 88 is coaxially mounted on the distal end 81B of the hypotube 81 as in the manner shown in FIG. 9B. Fill holes 93 are provided in the wall of the distal end 81B of the hypotube 81 along the section of hypotube enclosed within the balloon member 88. During the application, these fill holes 93 allow the passage of irrigation fluid into the balloon member 88. As the fluid pressure reaches up to inflation pressure of the balloon member 88, the balloon member is inflated. An exemplary inflation pressure range for the occlusion balloons can be given as 40 psi. However, for the therapeutic balloons, such pressure range can be as high as 200 psi.

As shown in FIG. 9C, a number of valve members are also provided over the inner wall of the distal end 81B of the hypotube 81. The valve members are attached over the perforations 85 as in the manner shown in FIG. 9C. Preferably, the valve members 94 are comprised of elastomeric membranes. These membranes 94 can be configured and dimensioned to withstand some threshold fluid pressure, such as the inflation pressure of the balloon member 88.

In applications, any pressure over this threshold pressure breaks open these membranes 94, i.e., activates valves 94, and delivers the irrigation fluid, through perforations 85, into the body locations. The fluid delivery can be also provided through leakages from both optional the slits (not shown) in the balloon member 88 and the gaps between the coil turns 86. As in the previous embodiment, the catheter 80C can be advantageously used for occlusion and irrigation therapies.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A medical wire comprising:

an elongate body having distal and proximal sections constructed from a nickel titanium alloy material, said distal section being constructed from a first nickel titanium alloy material exhibiting transformational superelasticity and having substantially constant stress values over a range of recoverable strains from about 1% to about 8%, said proximal section being constructed from a second nickel titanium alloy material having a modulus which is higher for a given strain than said first alloy material.

* * * * *